United States Patent [19]

Golberstein

[11] Patent Number: 4,770,536
[45] Date of Patent: Sep. 13, 1988

[54] REFLECTIVE PHOTOMETRY INSTRUMENT

[76] Inventor: Moshe Golberstein, 2100 Drew Ave. South, Minneapolis, Minn. 55416

[21] Appl. No.: 937,367

[22] Filed: Dec. 4, 1986

[51] Int. Cl.$^4$ .......................................... G01N 21/47
[52] U.S. Cl. ..................... 356/371; 356/446
[58] Field of Search ................ 356/371–445, 356/446, 448; 250/571, 572

[56] References Cited

U.S. PATENT DOCUMENTS

| | | | |
|---|---|---|---|
| 4,311,393 | 1/1982 | Bartke | 356/407 |
| 4,332,477 | 6/1982 | Sato | 356/371 |
| 4,368,983 | 1/1983 | Bennett | 356/445 |
| 4,390,278 | 6/1983 | Inoue | 356/392 |
| 4,425,041 | 1/1984 | Nishiyama | 356/371 |
| 4,427,295 | 1/1984 | Nishiyama | 356/371 |
| 4,443,106 | 4/1984 | Yasuda | 356/357 |
| 4,443,107 | 4/1984 | Alexander et al. | 356/373 |
| 4,465,350 | 8/1984 | Westerberg | 354/4 |
| 4,468,775 | 8/1984 | Meyer et al. | 372/92 |
| 4,511,800 | 4/1985 | Harbeke et al. | 356/371 X |
| 4,538,912 | 9/1985 | Shaw, Jr. | 356/366 |
| 4,538,913 | 9/1985 | Anthon | 356/371 |
| 4,552,458 | 11/1985 | Lowne | 356/446 |
| 4,676,653 | 6/1987 | Strohmeier et al. | 356/446 |

Primary Examiner—Eugene R. LaRoche
Assistant Examiner—David Mis
Attorney, Agent, or Firm—James V. Harmon

[57] ABSTRACT

A relative reflectivity photometry instrument is provided for measuring surface reflectance as a measure, for example, of surface roughness of a specimen. The instrument includes a housing or barrel having a source of light at one end and a pair of photosensors such as photodiodes at the other end, one of which is positioned to receive rays directly from the light source and the other of which is oriented in a different direction to receive light only after the rays from the light source have struck the specimen and are scattered back onto the second sensor. Typically, the light source is mounted at the top of a barrel with the photodiodes positioned at the lower end of the barrel. The photodiodes are provided with a central opening through which a portion of the bundle of rays passes onto the specimen and is thereafter reflected onto the photosensitive surface of the second diode. Circuitry is provided for amplifying and comparing the signals received the first and second photosensitive surfaces. The comparing circuit can comprise a divider circuit for establishing a ratio between the signals from the first and second photodiodes.

16 Claims, 2 Drawing Sheets

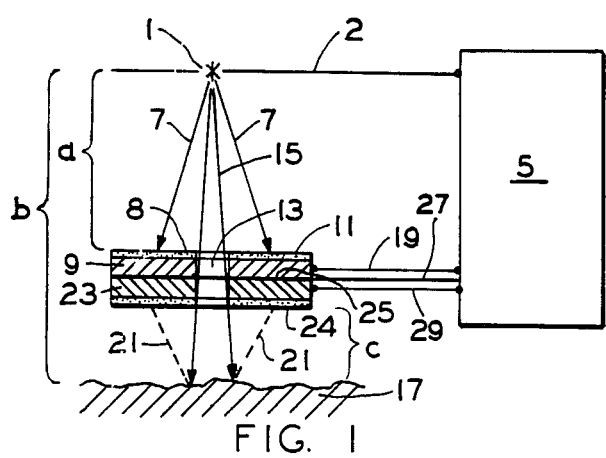
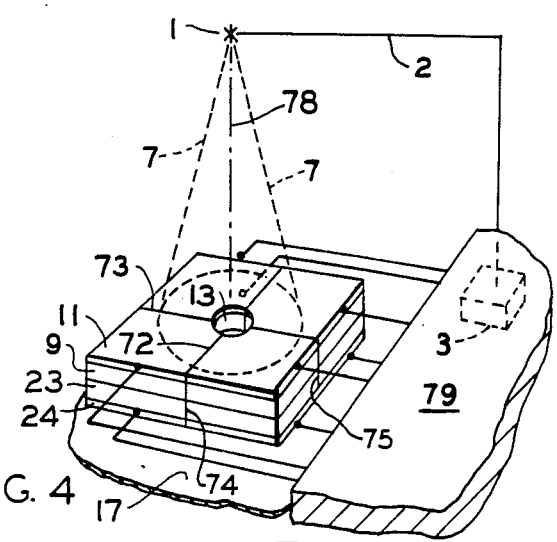
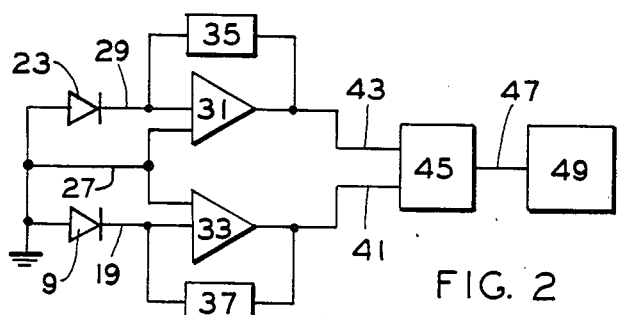
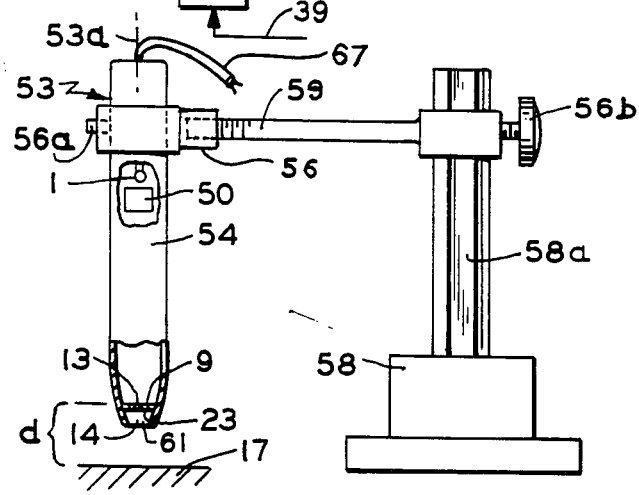
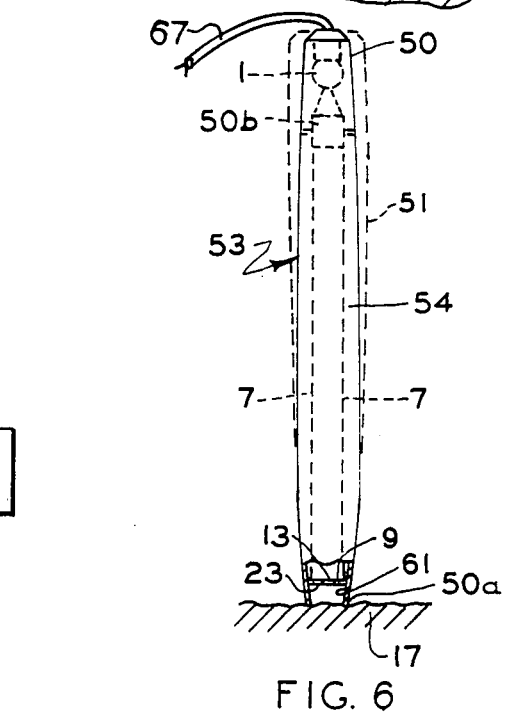
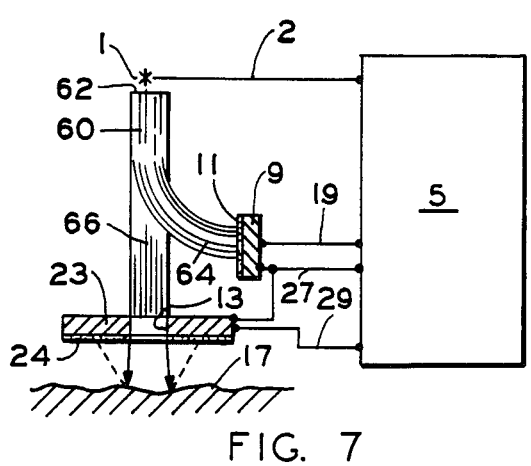

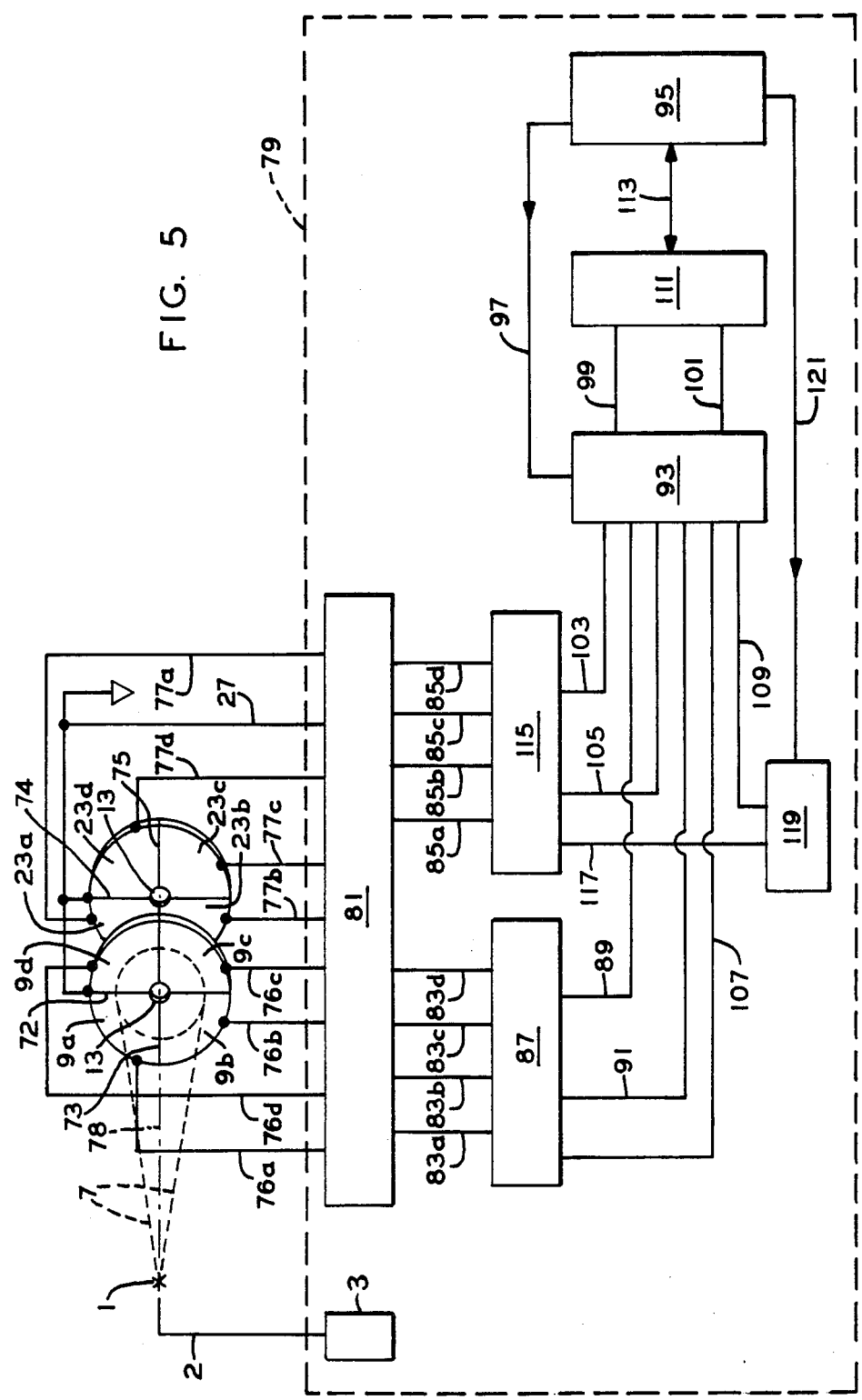

REFLECTIVE PHOTOMETRY INSTRUMENT

BACKGROUND OF THE INVENTION

Of the many instruments proposed for measuring surface reflectance optically, none are completely satisfactory with respect to cost, size, portability and accuracy. Most, if not all, prior instruments require an optical system that includes many lenses and other costly components such as half-silvered mirrors, monochromatic light sources, and special alignment schemes which increase cost, size, bulk, and reduce portability. For example, one prior instrument is called a Gloss meter or total integrated scatter instrument. In this instrument, light from an incandescent bulb passes through columnating lenses and is focused on the specimen at an oblique angle. The light is reflected away from the surface at an oblique angle into an optical system comprising additional lenses and a half-silvered mirror which reflects a portion of the light to the first photosensitive element and allows the rest to pass on to a second photosensitive element. Such an instrument requires a multitude of lenses that increase its size, bulk and cost. Moreover, the accuracy of the measurement depends strongly upon wavelength of light in a known relation to surface reflectance, the instrument's ability to separate between specular and diffused reflectivity components of the scattered light, the quality of the lenses and the relative alignment of the components. To overcome these disadvantages, it is a primary object to provide an accurate and highly effective and portable instrument of reduced size, complexity and bulk, for measuring surface reflectance. A further object is to provide a surface reflectance measuring instrument with component parts constructed and arranged to inherently produce an output that represents surface reflectance accurately and wherein certain ambient or environmental factors cancel each other out. A further object is to provide a new method by which the ratio of the light reflected from a specimen is compared with light of a known magnitude reflected from a similar specimen under the same illumination conditions by means of a reference photosensor with a provision through which the output of the instrument will be largely independent of the optical power coupled onto the surface. A further object is to provide an improved instrument of the type described which lends itself to the production of an inexpensive hand held instrument of small size as well as to the production of stationary or motorized scanning instruments or the production of instruments that will provide an output such as an alarm indicating whether the specimen meets expected reflectance criteria.

These and other more detailed and more specific objects of the invention will be apparent in view of the accompanying detailed description setting forth by way of example a few of the various ways within the scope of the invention these objectives can be accomplished.

SUMMARY OF THE INVENTION

The invention provides an instrument for measuring surface reflectance of a specimen. The instrument includes a light source compatible with the specimen, e.g., an LED, laser diode or an incandescent light and photosensors compatible with the light source. A first photosensitive surface is positioned in optical relationship with the source to receive impinging rays directly from the source. A second photosensitive surface is positioned relative to the source and the specimen to receive rays reflected from the specimen. A supporting means is provided to establish the distance between (a) the source and the first surface, (b) the source and the specimen, and (c) the specimen and the second surface. A signal conditioning and comparing means is provided and connected to the first photosensitive and second photosensitive surfaces to establish a ratio between a signal received from the first and second photosensitive surfaces proportional to the ratio of the optical power incident to the first and second photosensitive surfaces and an output means such as a meter, alarm or the like is connected to the comparing means to thereby provide an indication of the surface reflectance of the specimen.

Refer now to the figures which illustrate the invention by way of example.

THE FIGURES

FIG. 1 is a schematic diagram illustrating one preferred form of the invention.

FIG. 2 is a schematic view of the circuitry used in connection with FIG. 1.

FIG. 3 is a side elevational view partly broken away of another form of the invention.

FIG. 4 is a diagrammatic view in perspective of another embodiment of the invention.

FIG. 5 is a schematic diagram of circuitry employed in connection with FIG. 4.

FIG. 6 is a side elevational view partly broken away of another form of the invention.

FIG. 7 is a combined schematic and side elevational diagrammatic view of another form of the invention.

DETAILED DESCRIPTION

The operation of the instrument is based upon relative reflectivity, namely on a known value of reflectivity of many types of specimens. Based on this knowledge of reflectivity, the invention utilizes the relative optical power incident to a first photosensitive surface from a light source and that reflected onto a second photosensitive surface from the specimen. While the instrument can be employed for a variety of uses, typical applications include but not limited to the surfaces of metals.

In its preferred form, the invention eliminates the need for many lenses, reduces complexity and alignment requirements but still provides accurate surface reflectance information. Thus it makes possible a cost effective alternative to presently available surface reflectance instruments.

The present invention is based upon the concept that a light source whether or not focused or columnated is picked up by two photosensors, one exposed directly to the light from the source and the other exposed indirectly after being reflected from the test specimen. In one preferred form of the invention, the specimen is illuminated through a hole present in the center of a photosensor. If the beam of light is relatively narrow, all or virtually all of the light reflected from the specimen under test will be scattered back onto the photosensor. This photonic energy scattered onto the photosensor is representative of the surface reflectance of the specimen under test. If it is known that a certain specimen when subjected to a particular industrial process that yields a certain quantity of surface reflectance, and if the specimen will be illuminated with a known light source which is positioned at a known angular relationship to the specimen, the specimen will reflect a quantity of light X. This quantity of light X, which is optical power is a reference figure for calibrating the instrument. Accordingly, from two signals, (a) one derived from a reference photosensor and (b) a second from a photosensor that receives scattered light from the specimen positioned at a known relationship to the light source, the relative surface reflectance is determined.

Refer now to FIG. 1. Illumination is provided by a light source 1 such as an LED, laser diode or any other convenient source of light including incandescent, gas discharge tube, etc. The particular type of light source used should be compatible with the specimen 17 under study as will be apparent to those skilled in the art. For example, an infrared source should not be used with a specimen that primarily absorbs infrared radiation. The light source 1 is wired by means of conductors 2 to any suitable power source that is included in signal conditioning circuit 5. Between the light source 1 and the specimen 17 is a pair of photosensors 9 and 23 mounted back-to-back with photosensitive surfaces 11 and 24 respectively facing in opposite directions, the photosensitive surface 11 facing the source of light 1 and the photosensitive surface 24 facing the specimen. A light aperture 13 which is common to photosensors 9 and 23, in this case substantially at the center, is aligned axially with the light coming from the light source 1. The light source 1 thus projects a light beam depicted by the envelope 7 illuminating the photosensitive surface 11 of the photosensor 9 over a defined area 8. The photosensor 9 intercepts the light envelope and serves as a reference photosensor. The reference photosensor 9 is connected to signal conditioning hardware 5 by means of conductor 19 and ground wire 27. The light aperture 13 at the center of the reference photosensor 9 and photosensor 23 allows the transmission of light within a smaller envelope 15 to pass through both photosensors to the surface of the specimen 17 under test. The light from the envelope 15 is scattered from the surface of specimen 17 under test onto the photosensitive surface 24 of the photosensor 23. The scattered light is depicted by an envelope 21. Photosensor 23 is connected to the signal conditioning circuit 5 by means of conductor 29 and ground conductor 27, the latter being a common ground. Through the use of suitable signal conditioning circuits depicted in FIG. 2, the information concerning the surface reflectance roughness of the specimen 17 under test is derived. It will be noticed that photosensors 9 and 23 are held in physical contact with one another and hence are always at the same temperature to assure accuracy and reproducibility of results.

Refer now to FIG. 2 that describes details of signal conditioning hardware 5 of FIG. 1. In the apparatus and method shown in FIG. 2, the surface reflectance as a measure of surface roughness of the specimen 17 is compared to a standard (not shown) having a known surface reflectance producing a specific scatter characteristic when illuminated with a light source 1 located in the same relationship to the surface of the standard as it would be located in relationship to the specimen 17. The derivation of the comparative measurement method will now be described. For the sake of description, it will be assumed that photosensors 19 and 23 are silicon photodiodes and that they are sensitive to the optical power projected from the light source 1 in FIG. 1. While any suitable pair of photosensors can be employed, the guiding rule for choosing photodiodes made of a particular material and constructed in a special manner as known to the skilled in the art, is mainly its responsivity to the light source 1 (FIG. 1). The photodiodes are in heat conductive relationship but insulated from one another electrically by means of at least one insulating layer simply shown by numeral 25 (FIG. 1). The photosensor 23 which intercepts scattered optical power from surface 17 is connected to an amplifier 31 by means of conductors 29 and common ground 27. Across the amplifier 31 there is a gain setting network 35, that may include a filter (not shown), the purpose of which is to remove AC signals, if any, produced by ambient illumination such as 60 Hz for example. Any suitable amplifier with more detailed connections apparent to those skilled in the art can be used if desired. The signal in output line 43 of the amplifier 31 will thus be a function of the photonic energy scattered from the surface of specimen 17 (FIG. 1) or a reference surface, and the optical power projected through aperture 13, depending whether the instrument is being used for calibration or measurement mode, onto photosensor 23. The reference photosensor 9 is connected to an amplifier 33 by means of conductor 19 and common ground 27. The gain of amplifier 33 is programmable by means of altering the feedback network 37 through a suitable programming signal provided by way of illustration through the signal line 39. The purpose for controlling the gain by adjusting the impedance of network 37 through a programming signal 39 is to duplicate the scatter characteristic derived from a reference surface illuminated by the same instrument positioned in a known geometrical relationship to the reference surface. Therefore, when the instrument is being calibrated, a reference surface illuminated by the light source 1, will reflect scattered light onto photosensor 23 causing a corresponding signal 43. At this point in time, the operator (not shown), which can be a person or a device programmed to perform calibration will produce a signal via line 39 to equalize the output 41 which is being derived from the optical power intercepted by the reference photosensor 9. Signals 41 and 43 are connected to a comparing circuit such as a ratio circuit 45. The signal 43 is a numerator and the signal 41 is the denominator of the ratio. The output of the ratio circuit 45 which divides signal 43 by signal 41 is depicted by numeral 47 can be in a digital or analog form. Once signals 43 and 41 are equalized as a part of the calibration procedure, the output 47 will be equivalent to 1. It can be seen therefore that the output 47 will be largely independent of the optical power produced by the light source 1 (FIG. 1). The calibration now is complete. The instrument can be used to test a specimen 17 which was made of the same material and processed by the same process as the reference surface. During use, the instrument will be positioned in the same manner in reference to the specimen 17 as it was positioned in toward the reference surface. Signal changes in the output line depicted by numeral 47 will indicate whether the surface reflectance as a measure of surface roughness of specimen 17 is higher or lower than that of the reference surface. For example, if the surface roughness of specimen 17 is higher than the surface roughness of the reference surface, then the output 47 will be lower than 1. If the surface roughness of specimen 17 is lower than the surface roughness of the reference surface, the ratio will be higher than 1. An appropriate scale can be used to quantify the deviations of surface roughness from 1. The signal 47 can be connected to a display 49 or other audible or visible indicator providing the user with alarms or information indicative of acceptable surface roughness conditions based on operators criteria. In this regard, one can also say that the ratio signal 47 is largely independent of the variations of optical power produced by the light source 1. This is true since the signals 43 and 41 are also proportional to the optical power projected by the light source 1. This type of an operation of calibration and test can be performed for many types of materials subjected to many types of processes. The programming signal 39 can be tabulated and recorded by the operator for ease of instrument application. Accordingly, accurate readings corresponding to surface roughness are provided.

Refer now to FIG. 6 which illustrates instrument 53 which may be a hand-held instrument in accordance with the present invention generally similar in shape and size to a fountain pen. The same numerals refer to corresponding parts already described. Conductors 2, 76, 27 and 77 pass through a cord 67. In this case, the instrument 53 consists of a rather tall, thin, hollow barrel 54 having an upper end 50 supporting the light source 1. As already described, the uncolumnated light from the source 1 falls onto the reference photosensor 9 within a cone depicted by envelope 7. The barrel 54 of instrument 53 is provided with an opening at its lower end surrounded by a supporting rim 50a which rests during operation on the test specimen 17. The supporting rim 50a as shown is oriented at right angles to the axis of the barrel 54 thereby orienting the axis of the light envelope 7 perpendicular to the surface of the specimen 17.

The instrument is held manually in contact with the surface 17. The supporting rim 50a can be composed of some substance such as Teflon or other material that will not contaminate the surface 17. The internal wall 61 within the instrument below the photosensor 23 is preferably coated with a nonreflective coating that will prevent higher order defraction of scattered light onto the photosensor 23. The instrument 53 establishes three distances: the distance between (a) the light source 1 and the first photosensor 9, (b) between the light source 1 and the specimen 17 and (c) between the specimen 17 and the second photosensor 23. These distances are established by structural parts of the apparatus including the barrel 54 supporting the light 1 and photosensors 9 and 23 and the supporting rim 50a. The instrument 53 can be tilted back and forth as indicated by broken line 51 to seat the supporting rim 50a firmly on the specimen 17.

Using the hand-held instrument, one can perform a calibration or alignment operation at a certain angular relationship between reference or test surface 17 and the instrument 53. Therefore, the operator will tilt the instrument randomly, while the programmable circuit 95 will monitor signals 103 and 105. When signals 103 will satisfy the predetermined alignment conditions, signals 109 and 107 will be fed to the programmable circuit 95. Moreover, using the hand-held instrument, one can perform a calibration sequence of operations by means of commanding the programmable circuit 95 in FIG. 5 to take data only at a certain orientation between the instrument 53 and the reference surface. In this case, the instrument 53 will be programmed to accept signals 103 and 105 only under the same orientation conditions between surface 17 and the instrument 53. This is possible due to the fact that signals 103 and 105 describe the angular relationship between the surface 17 and the light source 1.

Refer now to FIG. 3, which illustrates another form of the instrument embodying the invention with the same numerals indicating parts described above. The instrument indicated generally at 53 comprises an upright cylindrical barrel or tube 54 within which the light source 1 is mounted near the top. The photosensors 9 and 23 with a central aperture 13 are mounted near the lower end of the barrel which has an opening 14 at its lower end above the surface of the specimen 17. The barrel 54 is supported upon a bracket 56 secured thereto by means of screw 56a. Bracket 56 is attached to an arm 59 which is threaded to accommodate bracket 56. The arm 59 is secured by means of hand wheel 56b to the stand 58 having a post 58a to provide a supporting fixture. Therefore by hand wheel 56b one can change the vertical position of the barrel 54, and by bracket 56 one can change the angular position of the barrel as relates to the surface of the specimen, or a reference surface. In this way, the instrument 53 having an optical axis 53a can be used in a desirable and controllable orientation toward the surface of specimen 17, and at a controlled distance d between the surface 17 and photosensor 23. Depending on the optical power distribution from the light source 1, one may add a lens 50b that will help to couple more light through the aperture 13 to the surface 17. The connections of photosensors 9 and 23 to the general signal conditioning hardware 5 (FIG. 1) are provided via a cable 67. For clarity of illustration, the wires 19, 27 and 29 within cable 67 and photosensors 9 and 23 are not shown in the barrel 54. Therefore, such a fixture can be used to calibrate and use the instrument described in FIGS. 1 and 2.

Refer now to FIG. 4 which illustrates a modified form of the invention and wherein the same numerals refer to corresponding parts already described. Light is provided by lamp 1 powered by drive circuit 3 which is wired to the lamp via conductor 2. Instead of using a single photodiode for photosensor 9 and a single photodiode for photosensor 23 as was illustrated in FIG. 1, each of the photosensors 9 and 23 is made out of four coplanar monolithic photodiode segments that are electrically insulated from each other and arranged around an optic axis 78 of the instrument. In the present case, these four quadrant photosensors or segments are modified to have a central and common aperture 13 essentially in the center of the intersection lines 72 and 73 of the quadrants of photosensor 9. Lines 74 and 75 separating photosensor 23 into four electrically isolated photodiodes distributed around aperture 13 are partially obstructed from view in this figure. Lines 74 and 75 may or may not coincide with the extended lines 72 and 73. As in FIG. 1, the light source 1 is mounted in such way that it projects a light within an envelope 7 along an axis or symmetry line 78 perpendicular to the photosensor 9. As illustrated in FIG. 5, photosensor 9 is connected via four lines 76a, 76b, 76c and 76d that correspond to photodiodes 9a, 9b, 9c and 9d within photosensor 9, to signal conditioning hardware 79. Photosensor 23 is connected via four lines 77a, 77b, 77c and 77d that correspond to the four photodiodes 23a, 23b, 23c and 23d to signal conditioning hardware 79. Other connections to the signal conditioning hardware include a common ground line 27 and lines 2 to supply current to light source 1. The construction and operation of the invention as shown in FIG. 4 will now be described with a reference to the signal conditioning hardware 79 that is shown in FIG. 5.

As shown in FIG. 5, the photosensors 9 and 23 are separated for illustration purposes only. Signals 76a, 76b, 76c, 76d, 77a, 77b, 77c, and 77d are fed into an amplifier circuit 81 that amplifies the signals produced by the photodiodes of photosensors 9 and 23. As known to the skilled in the art, amplification can be performed by a single amplifier by means of sequencing the corresponding signals for amplification. However, for the ease and clarity of explanation, the circuit 81 contains eight amplifiers producing amplified signals 83a, 83b, 83c, and 83d, proportional to the optical power intercepted by photodiodes of the photosensors 9a, 9b, 9c and 9d, and 85a, 85b, 85c and 85d, proportional to the optical power intercepted by photodiodes of the photosensors 23a, 23b, 23c and 23d. Signals 83a, 83b, 83c, and 83d are fed into another circuit 87 producing two outputs 89 and 91. The output 89 corresponds to the relationship produced by the sum of signals 83b and 83d, minus the sum of the signals 83a and 83c. This relationship of amplified signal intercepted by photosensor 9 is one measure of the light source 1 alignment with the axis of the aperture 13. Signal 91 corresponds to the sum of signals 83a, 83b, 83c, and 83d. Means for the implementation of such summing functions are known to those skilled in the art.

The signals 89 and 91 are fed into the circuit 93 which can switch different inputs based on commands from an operator or from a programmable electronic circuit 95. The control of the programmable circuit 95 by an operator knowledgeable to operate the instrument or by a computer 95 is indicated by a signal line 97. Therefore, the signal 97 will allow the circuit 93 to produce two outputs 99 and 101 which will correspond to these signals 89 and 91, or 103 and 105, or 107 and 109. Signals 99 and 101 which according to the sequence of operations performed by the instrument will represent signals 89 and 91, are connected to a divider circuit that produces a ratio between signals 89 and 91. This ratio signal 113 will correspond to the angular orientation, i.e., the degree of alignment between light source 1, aperture 13 and photosensors 9 and 23. The ratio signal is fed to the operator or a programmable device 95.

A correction to the alignment of light source 1 to aperture 13 can be implemented mechanically, or mathematically by the operator or the programmable circuit 95. At the particular part of the sequence in which signal 113 represents the ratio between signals 89 and 91, where 89 is the numerator and 91 the denominator, the signal 113 is largely independent the optical power produced by the light source 1. Signals 85a, 85b, 85c and 85d which represent amplified optical power scattered from the surface 17 or a reference surface (not shown in this figure) are connected to the signal conditioning circuit 115 which, like the circuit 87, produces two output signals. The signal 103 corresponds to the sum of signals 85b and 85d minus the sum of signals 85a and 85c. Signal 105 represents the sum of signals 85a, 85b, 85c and 85d. Signals 103 and 105 are connected to circuit 93 which in the proper sequence of steps to operate the instrument, will feed these signals on lines 99 and 101 correspondingly to the ratio circuit 111, which is in turn connected to the programmable circuit or an operator simply labeled 95. This ratio will become largely independent of the variations of the optical power projected by the light source and it will indicate the alignment angle between the instrument and the surface 17 or the reference surface. If the photosensors 9 and 23, the aperture 13 and the light source are perfectly aligned along the symmetry axis 78 with photosensor perpendicular to the axis, the signals 83a, 83b, 83c and 83d will be essentially equal to each other, otherwise the ratio between signal 89 and signal 91 will represent a reference alignment error. For example, this means that if a surface were illuminated perpendicularly through the aperture 13, the axis of the instrument will be tilted by the alignment error, which in turn will affect the scatter characteristics of optical power reflected from the surface 17 or a reference surface. Therefore it will also be necessary to correct the reflected scatter characteristics as intercepted by photosensor 23. This is done by providing a mathematical correction with the programmable electronic circuit 95. This correction can be applied to the rest of the incoming signals by the operator or the programmable circuit 95.

Based on the signals 83a, 83b, 83c and 83d, circuit 87 also produces an output 107 that is proportional to the average power intercepted by the reference photosensor 9. Based on the signals 85a, 85b, 85c and 85d, circuit 115 produces signal 117 which is proportional to the average optical power intercepted by photosensor 23. Signal 117 is fed to circuit 119 in which it is corrected by signal 121 provided from the programmable circuit 95 or the operator. The correction signal 121 is based on the angular alignment between photosensor 23 and the surface of specimen 17 or a reference surface, and the alignment error between light source 1 and photosensor 9. The output of circuit 119 is signal 109. Signals 109 and 107 are fed via the switching network 93 and the ratio device 111 to the programmable circuit 95 or operator. The resultant ratio of the signals 109 and 107 will represent the surface reflectance as a measure of surface roughness of the specimen 17. This ratio will be largely independent of variations of the optical power projected from the light source 1. At first, one will use a reference surface at a known geometrical orientation to the instrument. The instrument is calibrated by storing the different alignment characteristics described above by the operator or a programmable circuit 95 which will equalize output signal 107 to the signal 109 (e.g., by use of memory in the programmable circuit 95 and signal 121). Thus the resultant ratio between signals 107 and 109 will be 1. If one will exchange the reference surface with a specimen 17 which was made of the same material and in the same manner as the reference, the ratio of the signal 109 over 107 will indicate the roughness characteristic.

Refer now to FIG. 7 which illustrates another form of the invention. In the instrument of FIG. 7, the light source 1 is mounted at the end of optical fiber(s) 60 in position to illuminate the fiber(s) at the top end 62. The fiber(s) are divided into two parts, 64 and 66, which are brought into proximity with the photosensor 23 and the photosensor 9 respectively. Preferably, the fiber(s) 66 are secured to the aperture 13 of the photosensor 23 with a suitable adhesive. It will be noticed that the photosensor 9 in this instance, does not have a central aperture. It is preferred that the photosensors 9 and 23 be located close together in heat conductive relationship reducing the possibility of temperature gradient between them. The same is true and evident from the description provided for photosensors 9 and 23 in FIGS. 1 and 4 in which it will be noticed that they are held in physical contact with one another and hence are always at the same temperature to assure accuracy and reproducibility of results. The light reflected from the specimen 17 under test will be intercepted by the photosensor 23. The signal conditioning hardware of FIGS. 2 or 5 can be used dependent on whether or not the photosensor 23 is a four quadrant photosensor.

Beside simplicity and accuracy, the instrument in accordance with the present invention has other advantages. No lenses or precision ground mirrors are essential to operation. An inexpensive light source can be provided in combination with an inexpensive voltage or current reference that need not be very stable. This is due to the ratio functions implemented by the instrument that reduce its sensitivity to variations in the voltage or current reference.

Moreover, the present invention provides most of the advantages of prior equipment and overcomes shortcomings thereof through a unique method of transmitting and receiving optical power. It therefore reduces the complexity of signal processing required to provide final results in describing surface roughness.

The invention also provides an opportunity to use a relatively small numerical aperture that easily separates specular and diffused reflectances, and by these means eliminates the need for Coblentz spheres previously used in commercially available total integrated scatter instruments. While the instrument of the present invention uses an aperture, its principle of operation is substantially different from the typical total integrated scatter instrument of the prior art which in operation is directly dependent on the relationship between the wavelength of the light source and the surface roughness of the specimen. Since the suggested configurations of the present invention have lower mass and bulk and more even mass distribution in the instrument, the invention will be more immune to vibration than those presently available instruments used for surface reflectance measurements.

Many variations of the invention within the scope of the appended claims will be apparent to those skilled in the art once the principles of the invention described above are understood.

What is claimed is:

1. An instrument for measuring reflectance of a specimen comprising,
   a light source compatible with the specimen,
   a first photosensitive surface in optical relationship with the source to receive impinging rays from said light source,
   a second photosensitive surface positioned relative to the light source and positionable with respect to a specimen to receive rays reflected from the specimen,
   supporting means to establish the distance between, (a) the light source and the first photosensitive surface, (b) the light source to the specimen, (c) the specimen to the second surface,
   circuit means connected to the photosensitive surfaces for comparing the signal from the first and second photosensitive surfaces and output means connected to the comparing means indicating the reflectance of the specimen,
   the first and second photosensitive surfaces are positioned in back-to-back alignment with an opening therethrough for the passage of light from the light source through the opening to the specimen whereby an envelope of rays from the light source will strike the first photosensitive surface directly and the second photosensitive surface after being scattered from the specimen.

2. An instrument for measuring relfectance of a specimen comprising,
   a light source compatible with the specimen,
   a first photosensitive surface in optical relationship with the source to receive impinging rays from said light source,
   a second photosensitive surface positioned relative to the light source and positionable with respect to a specimen to receive rays reflected from the specimen,
   supporting means to establish the distance between, (a) the light source and the first photosensitive surface, (b) the light source to the specimen, (c) the specimen to the second photosensitive surface,
   circuit means connected to the photosensitive surfaces for comparing the signal from the first and second photosensitive surfaces and output means connected to the comparing means indicating the reflectance of the specimen,
   said instrument has a barrel of sufficiently small size and weight to be held in the hand for application to said specimen for measuring the surface reflectance thereof and said output means comprises at least one indicator means mounted on said barrel and adapted to indicate the reflectance of the specimen.

3. An instrument for measuring reflectance of a specimen comprising,
   a light source compatible with the specimen,
   a first photosensitive surface in optical relationship with the source to receive impinging rays from said light source,
   a second photosensitive surface positioned relative to the light source and positionable with respect to a specimen to receive rays reflected from the specimen,
   supporting means to establish the distance between, (a) the light source and the first photosensitive surface, (b) the light source to the specimen, (c) the specimen to the second photosensitive surface,
   circuit means connected to the photosensitive surfaces for comparing the signal from the first and second photosensitive surfaces and output means connected to the comparing means indicating the reflectance of the specimen,
   said instrument comprises an hollow enclosure means; said light source is mounted at one end of said enclosure means and is adapted to direct rays of light toward the opposite end of said enclosure means, said first and second photosensitive surfaces are mounted within said enclosure means at the opposite end thereof from the light source with a space provided for allowing at least some of the rays from the light source to pass the first and second photosensitive means and to strike the specimen without impingement thereupon and said first surface is oriented in a first direction adapted to receive impinging rays directly from the light source and said second photosensitive surface being oriented in a different direction out of the path of the light rays emanating from the light source and adapted to receive light rays reflected from the specimen and said instrument includes a supporting member for holding the second photosensitive surface at a predetermined distance from said specimen when the supporting member is placed in contact with the specimen.

4. An instrument for measuring reflectance of a specimen comprising,
 a light source compatible with the specimen,
 a first photosensitive surface in optical relationship with the source to receive impinging rays from said light source,
 a second photosensitive surface positioned relative to the light source and positionable with respect to a specimen to receive rays reflected from the specimen,
 supporting means to establish the distance between, (a) the light source and the first photosensitive surface, (b) the light source to the specimen, (c) the specimen to the second photosensitive surface,
 circuit means connected to the photosensitive surfaces for comparing the signal from the first and second photosensitive surfaces and output means connected to the comparing means indicating the reflectance of the specimen,
 the photosensitive surfaces are supported in back-to-back relationship with a passage in the instrument allowing at least a portion of the rays from the light source to pass both photosensitive surfaces without impingement thereupon and thereafter strike the specimen.

5. The instrument of claim 3 wherein the photosensors are insulated from one another electrically by means of an interposed insulating layer positioned between them.

6. The instrument of claim 3 wherein the photosensors are in physical association with one another to be thereby in heat conductive relationship with one another to maintain both photodiodes at the same temperature to thereby assure accuracy and reproducibility of surface roughness readings.

7. The apparatus of claim 5 wherein the first and second photosensors are positioned adjacent to one another in a back-to-back relationship to form a sandwich structure and said first and second photosensors comprise photosensitive elements divided into photosensitive segments distributed radially about an optic axis passing from the light source to the photosensitive surfaces, a first conductor means connecting each of the segments of the first photosensor to a first signal comparing circuit, the second set of conductors connecting the segments of the second photosensitive surface to a second signal comparing circuit whereby through comparing the signals received from the segments of the photosensors, differences in the amount of light received by each segment can be detected and the detected differences in the signal strengths received by the signal comparing circuits is connected to an indicator means to notify the user of the axial orientation of the instrument with respect to the specimen.

8. The instrument of claim 5 wherein said photosensors comprise a pair of photodiodes mounted in back-to-back relationship and in heat conductive relationship to maintain them at substantially the same temperature to thereby improve the accuracy and reproducibility of the readings taken and said photodiodes having aligned openings extending therethrough allowing the passage of light through the openings to the specimen whereby an envelope of rays from the light source will strike the first photodiode directly and the second photodiode after being scattered from the specimen and said signal comparing means comprises a divider circuit wherein the signal from one photodiode is a numerator signal and the signal from the second photodiode is a denominator signal, said divider circuit thereby providing a resultant ratio as a measure of the relative surface reflectance which is largely independent of the optical power produced by the light source and thereby independent of changes in the reference voltage or current used to drive the light source.

9. An instrument for measuring reflectance of a specimen comprising,
 a light source compatible with the specimen,
 a first photosensitive surface in optical relationship with the source to receiving impinging rays from said light source,
 a second photosensitive surface positioned relative to the light source and positionable with respect to a specimen to receive rays reflected from the specimen,
 supporting means to establish the distance between, (a) the light source and the first photosensitive surface, (b) the light source to the specimen, (c) the specimen to the second photosensitive surface,
 circuit means connected to the photosensitive surfaces for comparing the signal from the first and second photosensitive surfaces and output means connected to the comparing means indicating the reflectance of the specimen,
 a fiber optic link comprising two or more fibers adapted to conduct light from said light source to said first and second photosensitive surfaces is provided, one end of said link being positioned adjacent the light source and the other end of the link being divided into two segments, one of which is positioned in light transmitting relationship with the first photosensor, the other segment of which is positioned in light transmitting relationship to the specimen whereby a predetermined portion of the light from the light source is transmitted to the first photosensitive surface and another predetermined portion of the light from the light source is transmitted to the specimen and said second photosensitive surface receives the light rays from said portion of the fiber link after being reflected from the specimen.

10. An instrument for measuring surface reflectance of a specimen comprising,
 an instrument enclosure having first and second ends,
 a light source at the first end of the enclosure, said light source being compatible with the specimen,
 a first and second photosensitive means comprising a pair of photosensors positioned in back-to-back relationship and connected together in heat conducting relationship at the opposite end of the enclosure,
 said instrument including a space for allowing a bundle of rays to pass the photosensors and to travel to a specimen adjacent the second end of the enclosure,
 the first photosensor being positioned in optical relationship with the source to receive impinging rays directly from the light source and the second photosensor being positioned to receive light rays from the light source only after being reflected from the specimen,
 said enclosure having supporting means therein to establish the distance between, (a) the light source at one end of the enclosure and the first photosensor, (b) the light source and the specimen and (c) the specimen and the second photosensor, amplification means connected to each of said photosensors and each of the said photosensors comprised of at least one photodiode, and a signal comparing means connected to the amplification means for comparing the amplified signals from the photosensors and thereby provide an indication of the surface reflectance of the specimen by comparing the relative optical power received by each of the photosensors.

11. The apparatus of claim 10 wherein the signal comparing means comprises a divider circuit adapted to establish a ratio between the signals from the first and second photosensors and the resulting ratio is largely independent of the variations in optical power produced by the light source.

12. An instrument for measuring surface reflectance of a specimen comprising first and second photosensitive surfaces, the first of which receives light directly from a light source such that light strikes the first photosensitive surface without reflection from another surface and the second of which receives scattered light directly from a test specimen such that the scattered light strikes the second photosensitive surface without reflection from another surface, conductors connected to the photosensitive surfaces to carry signals therefrom proportional to the optical power of the incident light thereon and a comparing circuit means coupled to the conductors for comparing the output signals and indicator means is connected to the circuit to provide an output signal designating reflectance of the specimen.

13. The instrument of claim 12 wherein the circuit is a dividing circuit to indicate the ratio of the signals.

14. The instrument of claim 12 wherein the second photosensor has an aperture therein to admit light to the specimen from the light source.

15. The instrument of claim 12 wherein the instrument is calibrated by measuring light scattered from a standard specimen of known composition and surface quality to provide a known surface reflectance and said circuit means include gain control means for selectively changing the magnitude of said output signal to correspond to the known surface reflectance of the test specimen to thereby calibrate the instrument.

16. The apparatus of claim 12 wherein at least one of said photosensitive surfaces is divided into a plurality of coplanar electrically insulated photosensor segments arranged around an optic axis of said instrument and circuit means is connected thereto for comparing an output signal of each segment to thereby derive the angular orientation of the coplanar segments to light incident thereto.

* * * * *